(12) United States Patent
Bauer et al.

(10) Patent No.: US 7,040,140 B2
(45) Date of Patent: May 9, 2006

(54) DEVICE FOR SUSPENSION OF A SAMPLE BODY

(75) Inventors: Thomas L. Bauer, Bad Homburg (DE); Albrecht Vogel, Stutensee (DE); Peter Krippner, Karlsruhe (DE); Manfred Wetzko, Schriesheim (DE); Christian J. Schmidt, Heidelberg (DE); Antonio Ruzzu, Karlsruhe (DE); Rolf Merte, Heidelberg (DE)

(73) Assignee: ABB Patent GmbH, Ratingen (DE)

( * ) Notice: Subject to any disclaimer, the term of this patent is extended or adjusted under 35 U.S.C. 154(b) by 0 days.

(21) Appl. No.: 10/716,130

(22) Filed: Nov. 18, 2003

(65) Prior Publication Data

US 2004/0108442 A1 Jun. 10, 2004

(30) Foreign Application Priority Data

Nov. 29, 2002 (DE) ................................ 102 55 696

(51) Int. Cl.
*G01N 27/62* (2006.01)
(52) U.S. Cl. ..................... 73/25.02; 267/160; 324/201; 324/204
(58) Field of Classification Search ................ 267/160; 73/25.02, 24.01, 31.05; 324/201, 204, 214
See application file for complete search history.

(56) References Cited

U.S. PATENT DOCUMENTS

| | | | | | |
|---|---|---|---|---|---|
| 3,815,018 | A | * | 6/1974 | Gast et al. .................. | 324/201 |
| 3,826,974 | A | * | 7/1974 | Kocache et al. ............. | 324/201 |
| 4,860,574 | A | * | 8/1989 | Maeda et al. ............... | 324/204 |
| 5,369,980 | A | * | 12/1994 | Kocache .................... | 73/25.02 |
| 5,932,794 | A | * | 8/1999 | Fabinski et al. ........... | 73/25.02 |
| 6,246,227 | B1 | * | 6/2001 | Hobby et al. ............... | 324/204 |
| 6,371,434 | B1 | * | 4/2002 | Becker et al. .............. | 248/610 |
| 6,739,179 | B1 | * | 5/2004 | Vogel et al. ................ | 73/25.02 |
| 6,876,124 | B1 | * | 4/2005 | Lin et al. .................... | 310/309 |

* cited by examiner

*Primary Examiner*—James McClellan
*Assistant Examiner*—Mariano Sy
(74) *Attorney, Agent, or Firm*—Michael M. Rickin; Paul R. Katterle

(57) ABSTRACT

A device for suspension of a sample body which rotates in space about a rotation axis which is in a fixed position or is related to a fixed position, as a function of the intensity of a measurement effect. In order to ensure that a sample mass is mounted in the device securely and such that it can rotate very largely without any lateral movement, the suspension, which has at least two springs, for the sample body is designed to be planar in a rest position.

13 Claims, 1 Drawing Sheet

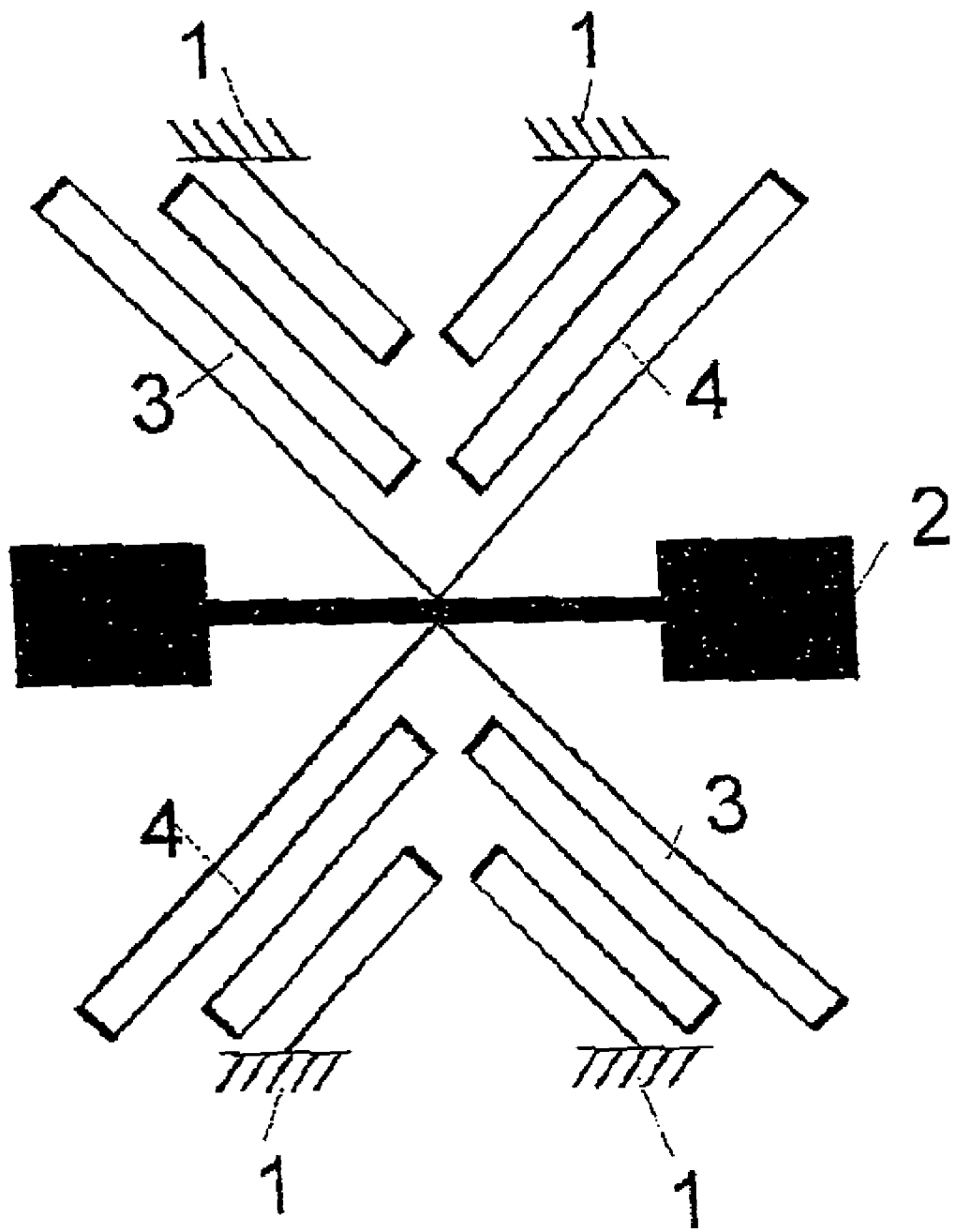

DEVICE FOR SUSPENSION OF A SAMPLE BODY

FIELD OF THE INVENTION

This invention relates to a device for suspension of a sample body which rotates in space about a rotation axis which is in a fixed position or is related to a fixed position, as a function of the intensity of a measurement effect.

DESCRIPTION OF THE PRIOR ART

Devices are known from the prior art, in which the sample mass is suspended by means of springs. Although torsions are also permissible in this case, these are, however, generally also accompanied by undesirable linear deflections.

In order to avoid linear deflections, a rotating suspension for a sample mass can also be provided by means of a fixed rotating shaft or a tension strip, although friction forces would need to be used to provide the rotating sliding bearing, or a three-dimensional arrangement of the elements would be required. In this case, in the function of automatic rotation back to an initial or null rotation position can often be represented only by complex physical interaction between springs.

Furthermore, a sample body suspension of this generic type may be a small precision part. The desired deflection, which is dependent on the measurement effect, requires precise suspension. In individual cases, this is a fine mechanism; and in special cases it is even a micromechanism.

The invention is thus based on the object of ensuring that a sample mass is mounted in said device securely and such that it can rotate very largely without any lateral movement, paying attention for the need for a physically small and compact shape at the same time.

SUMMARY OF THE INVENTION

The essence of the invention is in this case that the suspension, which comprises at least two springs, for the sample body is designed to be planar. This means that the springs are manufactured by cutting or etching them from a thin planar metal sheet. Alternatively, silicon may then also be used as the material. The spring turns are thus geometrically not formed or preshaped three-dimensionally, but effectively in a planar manner. The spring arrangement can thus be manufactured easily, and can easily be connected to the sample body. Even if the sample body is deflected in the form of a rotary oscillation, the springs are stressed such that they remain planar. They can thus be manufactured easily, while satisfying the fine-mechanical requirements to a very high degree.

The springs may in this case be composed in a particularly advantageous manner either of metal or glass or else, for example, of silicon. Since they are planar they can accordingly also be manufactured from a planar piece of material. Etching techniques can also advantageously be used for metal, glass or, in particular, for silicon as well.

In this context, a further advantageous refinement provides the sample body and spring to be composed of one material, or at least to be integrally connected to one another.

One enormous advantage is that high-precision springs can be produced, for example, by means of an etching technique and can be designed to be planar, in a corresponding manner.

A further advantageous refinement states that at least two springs are provided, with one of the springs being arranged above the sample body, and one being arranged underneath the sample body. This results in the good positioning, as described above.

A further refinement states that the spring force axes of the two springs run on a line.

A further advantageous refinement states that four springs are provided, with two of the springs being arranged above the sample body and two further springs being arranged underneath the sample body, such that the spring axes of two opposite springs in each case run on a line, and the two lines which are produced by four springs are approximately at right angles to one another. A torque acting on the rotation axis can then produce a torque that results in the measurement effect, and can hence produce a rotational deflection of the sample body. Once the torque is removed, however, the sample body returns back to its original position, as determined by the springs. Furthermore, this results in maximum spring stiffness with regard to undesirable linear deflection of the sample body.

A further advantageous refinement states that the device is a paramagnetic oxygen measurement device, and the sample body is dumbbell-shaped. This allows the stated advantages and functions to be implemented in a suitable manner.

A further advantageous refinement states that the springs are suspended such that their main spring axis is at right angles to the line of force of the suspension.

In a further refinement, the springs are suspended in a suspension frame which is arranged around the sample body. This results in a secure, fixed reference position for the original position of the sample body.

In a last particularly advantageous refinement, the springs are at the same time used to provide electrical supply leads to the sample body. This results in advantageous, multifunctional function integration, which leads to the sample body being mounted such that it can be rotated easily and otherwise without friction. This also critically improves the measurement result and the measurement sensitivity.

DESCRIPTION OF THE DRAWING

The only drawing FIGURE shows one exemplary embodiment for the present invention.

DESCRIPTION OF THE PREFERRED EMBODIMENT(S)

The only drawing FIGURE shows only the immediate functional environment of the sample body 2. This corresponds to a dumbbell of an oxygen measurement device that is based on the paramagnetic measurement principle. The measurement effect produces a torque, which is dependent on the partial pressure, on the dumbbell. The dumbbell is in this case held by four springs in the manner according to the invention, and the springs are arranged or suspended in a holding or mounting frame 1. The four springs are split into two so-called spring packs, with two of the springs being arranged above the sample body and two further springs being arranged underneath the sample body, such that the spring axes of two opposite springs in each case run on a line, and the two lines which are produced by four springs are approximately at right angles to one another.

Two springs, which are formed on two different sides of the rotation plane that is formed by the dumbbell movement and which are aligned on a common axis in each case form a so-called spring pack 3 or 4, respectively. The FIGURE shows that the axis on which two springs are in each case aligned to form a spring pack 3 or 4, is not the elongation axis or direction in which the springs would normally be tensioned directly. This clearly shows the effect according to the invention, that is to say that their spring force direction is not parallel either to the sample body or to the rotation axis. The spring force directions are equivalent to the stated elongation directions.

This results in the advantage, as already described above, of minimizing transverse deflections.

The individual springs may in this case also at the same time have the electrical function of providing the electrical power supply and/or the output for measurement signals, in addition to the pure spring function. Since the spring packs or the individual springs of the spring packs 3 and 4 act at the central rotation point, electrical contact that is made in this way avoids any additional restriction to rotation.

One important feature in this case is that the precision of planar springs or spring packs has been found to be particularly advantageous in this case because, on the one hand, they can be produced by means of a high-precision etching technique and, on the other hand, a high degree of manufacturing precision can be achieved thus assisting precision sample body suspension, and thus making it possible to achieve precise measurement sensitivity.

This spring configuration allows arrangements to be produced whose geometric dimensions are in the micromechanical range.

It is to be understood that the description of the preferred embodiment(s) is (are) intended to be only illustrative, rather than exhaustive, of the present invention. Those of ordinary skill will be able to make certain additions, deletions, and/or modifications to the embodiment(s) of the disclosed subject matter without departing from the spirit of the invention or its scope, as defined by the appended claims.

What is claimed is:

1. A measurement device comprising:
   a plurality of springs, each of said springs having an elongation axis and comprising a connecting leg connected to a plurality of turns, wherein in each of said springs, said connecting leg does not extend in the same direction as said elongation axis;
   a sample body held by said connecting legs of said springs so as to be rotatable about a rotation axis as a function of the intensity of a measurement effect;
   wherein a first pair of said springs are disposed on opposite sides of said sample body, respectively, with their connecting legs being substantially aligned along a first axis;
   wherein a second pair of said springs are disposed on opposite sides of said sample body, respectively, with their connecting legs being substantially aligned along a second axis; and
   wherein said first and second axes are disposed at approximately right angles to each other.

2. The measurement device of claim 1 wherein said springs are flat.

3. The measurement device of claim 2, wherein said springs are composed of metal.

4. The measurement device of claim 2, wherein said springs are composed of silicon.

5. The measurement device of claim 2, wherein said springs are composed of glass.

6. The measurement device of claim 1, wherein said sample body and said springs are composed of the same material.

7. The measurement device of claim 1, wherein said sample body and said springs are Integrally joined together.

8. The measurement device of claim 1, wherein said measurement device is a paramagnetic oxygen measurement device, and said sample body is dumbbell-shaped.

9. The measurement device of claim 1, wherein said springs are suspended in a suspension frame which is arranged around said sample body.

10. The device of claim 1, wherein said springs provide electrical supply leads to said sample body.

11. The device of claim 1, wherein said springs are formed from a thin metal sheet by cutting.

12. The device of claim 1, wherein said springs are formed from a thin metal sheet by etching.

13. The device of claim 1, wherein in each of said springs, said connecting leg is disposed at a right angle to said elongation axis.

* * * * *